United States Patent [19]

Regan

[11] 3,958,941
[45] May 25, 1976

[54] APPARATUS FOR MEASURING CONTENT OF ORGANIC CARBON

[75] Inventor: Michael Daniel Regan, Medway, Mass.

[73] Assignee: Sybron Corporation, Rochester, N.Y.

[22] Filed: Feb. 6, 1975

[21] Appl. No.: 547,622

[52] U.S. Cl. .......................... 23/253 PC
[51] Int. Cl.² .................................. G01N 31/12
[58] Field of Search ............... 23/253 PC, 230 PC

[56] References Cited
UNITED STATES PATENTS

| | | | |
|---|---|---|---|
| 3,287,088 | 11/1966 | Seevers | 23/230 R |
| 3,535,087 | 10/1970 | Hart et al. | 23/253 R |
| 3,854,877 | 12/1974 | Csaky et al. | 23/253 PC |

OTHER PUBLICATIONS

Soier et al., Photochemical Method of Determining Organic Carbon, Hydrochemical Materials, vol. 46, p. 111, Novocherkassh Hydrochemical Institute, U.S.S.R.

*Primary Examiner*—Robert M. Reese
*Attorney, Agent, or Firm*—Theodore B. Roessel; J. Stephen Yeo

[57] ABSTRACT

Apparatus for the quantitative determination of organic carbon dissolved in water and aqueous solutions. A sample is exposed to ultraviolet radiation which oxidizes the carbon content of any organic material contained therein to carbon dioxide. The amount of carbon dioxide generated is measured by apparatus which eliminates interference from other substances.

9 Claims, 3 Drawing Figures

APPARATUS FOR MEASURING CONTENT OF ORGANIC CARBON

BACKGROUND OF THE INVENTION

The invention is directed toward the measurement of organic carbon and more particularly concerns the measurement of the amount of organic carbon in aqueous solution. In pollution abatement, medical, and industrial processing situations, for examples, it is often necessary to determine the amount of organic carbon contained in water and aqueous solutions.

The prior art usually requires a combustion step at high temperatures, or requires alternatively, expensive highly purified reactants and/or carrier gases. The resulting carbon products, which may include $CO_2$, $CO$ or $CH_4$, are then fed into a measuring device wherein the carbon products are analyzed by such complex measuring systems as infrared spectrophotometry, flame ionization or nephelometry. It will be appreciated that presently available apparatus for the measurement of organic carbon in water are either extremely slow and cumbersome or involve highly sophisticated and expensive equipment.

Soier et al. have described apparatus which uses ultraviolet radiation to oxidize organic carbon into carbon dioxide which is then measured to determine the amount of organic carbon originally in the sample. (Photochemical Method of Determining Organic Carbon, Hydrochemical Materials, Vol. 46, pg. 111, Novocherkassh Hydrochemical Institute, USSR). A sample is funneled into a quartz chamber wherein it is exposed to ultraviolet radiation from a lamp external to the chamber. Organic carbon in the sample is oxidized into carbon dioxide. Purified atmospheric air is pumped through the chamber to transport the generated carbon dioxide to a coulometer which is arranged to measure the quantity of electricity produced by a chemical reaction of the carbon dioxide. Alternatively, volumetric titration may be used for the measurement.

Soier's apparatus exhibits the prior arts disadvantages which limits its utility as a field instrument and capacity for rapid repetitive tests. For example, Soier uses catalyzers maintained at 700°C in the air stream; and further he boils the sample. He does not provide a means to circulate the sample. A condenser using tap water flow is required because of the high temperature. A rather large sample of 30 ml. is used and must be removed from the apparatus before another sample can be introduced by a funnel. Required irradiation time is in the order of three hours unless a sensitizer such as atomic mercury is used.

It would, therefore, be highly desirable for an apparatus to be provided to determine the content of organic carbon in water without the requirement of high temperatures, catalysis, highly purified gases or other materials that may produce an unstable and undesirable background.

SUMMARY OF THE INVENTION

Apparatus is disclosed for measuring the amount of dissolved organic carbon introduced into a quantity of carrier water. An ultraviolet lamp is arranged with a first housing so as to irradiate the interior of the first housing. A second housing has measuring means for measuring the amount of any carbon dioxide in the second housing. An air loop connects the first housing to the second housing so as to transfer a portion of carbon dioxide generated in the first housing to the second housing. A first water loop circulates carrier water through the first housing, so that dissolved organic carbon introduced into this water loop will be irradiated within the first housing, generating carbon dioxide, a portion of which is transported to the second housing by means of the air loop. The measuring means senses the carbon dioxide which is representative of the amount or organic carbon introduced into the apparatus. The ultraviolet lamp is preferably internal to the first housing. The air loop may be driven by an eductor common to the air loop and the first water loop. The sample of dissolved carbon may be introduced to the first water loop through a rubber septum by means of a syringe and needle.

The measuring means may be a resistivity cell connected to a resistivity meter. The output of the resistivity meter may then be connected to a non-linear amplifier.

An arrangement for cleaning and purifying the carrier water includes a second water loop controlled by a valve, which may be activated by electrical timing circuitry.

BRIEF DESCRIPTION OF THE DRAWINGS

Advantages of the invention will become apparent upon reading the following detailed description and upon reference to the drawings, in which.

While the invention will be described in connection with a preferred embodiment and method, it will be understood that it is not intended to limit the invention to that embodiment and method. On the contrary, it is intended to cover all alternatives within the scope of the invention.

DETAILED DESCRIPTION OF THE INVENTION

It is known that by providing ultraviolet radiation to expose a variety of organic compounds dissolved in water and aqueous solutions in the presence of oxygen containing gas such as air, the carbon atoms of the compounds are oxidized producing carbon dioxide ($CO_2$). The resulting carbon dioxide can be measured by various means. However, to eliminate interferences from substances other than the $CO_2$ derived from the test sample, additional cleaning and separation apparatus is desired.

Figure 1:
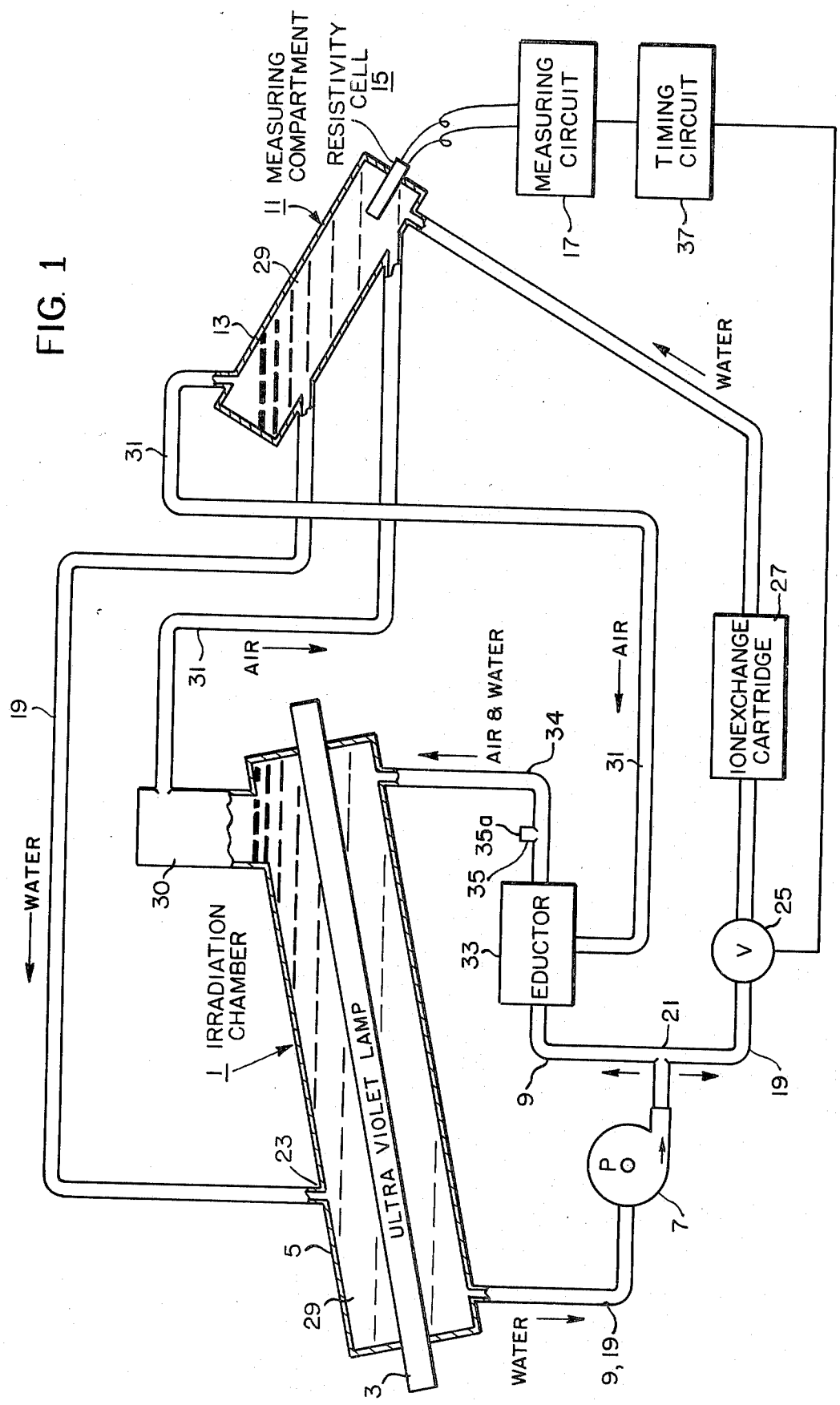
FIG. 1 is an overall diagram in partial cross section of apparatus for determining the amount of organic carbon in aqueous solution or in water according to the preferred embodiment of the present invention.

In the preferred embodiment as shown in FIG. 1, an irradiation chamber 1 is provided for irradiating a test sample with ultraviolet radiation. The irradiation chamber 1 includes an ultraviolet lamp 3 preferably mounted within a first watertight housing 5 so as to obtain maximum radiation from the lamp. The housing 5 is preferably constructed from a copper tube which is tin lined to prevent contamination of the water. A tube 2 inches in diameter and 30 inches long is suitable for a 1 milliliter sample and a standard length lamp.

Ultraviolet radiation is radiant energy within the wavelength range of approximately 10 to 380 nanometers. Radiation in the wavelength band of approximately 170 to 210 nanometers was found to be preferred for oxidizing organic carbon, however, there is not a sharp demarkation at the band edges, as the indicated effect is produced to a lesser extent by shorter and higher wavelengths. Therefore, for the most efficient operation the lamp 3 should emit ultraviolet radiation in the preferred wavelength range of 170 to 210 nanometers. Many commercially available lamps, such as the 40 watt, Model P247 Al-Bac lamp manufactured by Ultradynamics Corp. of Paterson, New Jersey, are suitable.

A pump 7 circulates water through a first water loop 9 which includes the irradiation chamber 1 thereby circulating the water through the chamber.

A measuring compartment 11 is provided for determining the amount of $CO_2$ generated. The measuring compartment 11 includes a second watertight housing 13, preferably constructed of polyvinylchoride, and containing a resistivity cell 15. Resistivity cells are known in the art and are sold by Barnstead Company among others. A measuring circuit 17 may be connected to the cell to calculate the representative amount of organic carbon.

A second water loop 19 connects the measuring compartment 11 to the first water loop 9 by means of a "tee" fitting 21 and a connector 23 to irradiation chamber 1. The pump 7 is common to both water loops 9 and 19. The second water loop 19 is controlled by a water valve 25 and contains a mixed bed ion exchange cartridge 27. The water valve 25 may be of the solenoid type so as to be controlled electrically.

The irradiation chamber 1, measuring compartment 11, and first and second water loops 9, and 19 are substantially filled with fluid 29 preferably distilled water which is used as a carrier media for the sample later to be introduced. A small air space 30 of say 100 ml. is maintained above the irradiation chamber 1 so as to provide oxygen. Another oxygen containing gas may be used in place of air.

The irradiation chamber 1 and the measuring compartment 11 are interconnected by a closed air loop 31 driven by an eductor 33 in the fist water loop 9. Polypropylene tubing is suitable for constructing the three loops. Tubing 34 between the measuring compartment and the eductor is common to both the first water loop 9 and the air loop 31.

In order to be able to measure the minute amounts of $CO_2$ dissolved in water, it is necessary that the carrier water 29 is absolutely pure, making a special cleaning cycle desirable. In the cleaning cycle, water valve 25 is open allowing the carrier water 29 to be circulated through the system to be cleansed by the mixed bed ion exchange cartridge 27, which removes all ionized material from the carrier water 29. Many commercially available ion exchangers leach out unwanted organic matter. An ion exchanger using a mixed bed resin having a minimum of leaching, such as that sold as XE277 by Rohm and Haas Co. of Philadelphia, Pa., should be used. In the preferred embodiment, during the cleaning cycle the ultraviolet lamp 3 is turned on and irradiates the carrier water 29 thereby converting all traces of leached organic material into $CO_2$. Most of the resulting $CO_2$ is removed by the ion exchanger 27.

It is conjectured that the ultraviolet radiation converts some of the oxygen contained within air space 30 into ozone. Ozone is chemically very active and reacts appreciably with any carbon present. There may also be direct ultraviolet oxidation of the organic carbon into $CO_2$. In any case, the organic carbon is converted in carbon dioxide. The electrical resistance of the carrier water 29 will increase as the water is purified. The cleaning process may be monitored by a resistivity or conductivity cell 15 and measuring circuit 17.

After the cleaning of the carrier water 29, the instrument is ready to measure the organic carbon in a test sample. The valve 25 is closed removing the ion exchanger 27 from the system and isolating the measuring compartment 11 from the first water loop 9. The pump 7 remains on, circulating the carrier water 29 through the first water loop 9, including the irradiation chamber but not the measuring compartment 11. A known volume of 1 milliliter of test sample volume, for example, is introduced into the first water loop 9 by via sample input port 35. The sample input ports 35 may include a rubber septum 35a in which case the sample of dissolved organic carbon may be injected by a syringe and needle. The sample is circulated from the input port 35, through the irradiation chamber wherein the organic compounds of the sample are exposed to ultraviolet light. The organic carbon dissolved in the sample is converted in carbon dioxide.

Eductor 33 in air loop 31 passes a recirculating air stream through the irradiating chamber 1 and measuring chamber 11. One purpose of air loop 31 is to isolate any non-gasous substances contained within the sample from the measuring chamber 11 thereby preventing interferences with the measurements. The air stream sweeps some of the $CO_2$ through the air loop 31 into the measuring compartment 11 equalizing the carbon dioxide concentration in the water in the radiation chamber with that of the water in the measuring chamber. To minimize equilibrium time, measuring housing 13 should be smaller than irradiating housing 5. A 1 inch diameter tube, 6 inches long, is suitable. Both housings 5 and 13 are tilted to assure turbulance in the system for a satisfactory mixture of gas and water.

A property of carbon dioxide is to decrease the resistance (or conversely to increase the conductivity) of water in which it is dissolved. The resistance cell 15 measures the resistance of the water in the measuring chamber 11. The resistance is a function of the concentration of the $CO_2$ in the water and hence can be related to the concentration to the organic carbon in the original sample. The presence of $CO_2$ in the water will lower the resistance in a known manner.

With a fixed concentration of carbon dioxide in solution the resistance of the water will vary with temperature. This effect is pronounced at high resistance conditions. Pump and lamp operation will cause temperature changes sufficient to affect the resistivity of a water temperature to an extent that compensation is desired. Compensation made be obtained by mounting thermistors within the resistivity cell 15. These cells are known and are commercially available. I used a Barnstead B51 cell which was connected to measuring circuit 17.

In keeping with the invention, the measuring circuit 17 may be used to calculate the amount of organic carbon present in the sample as a function of the resistance.

Figure 2:
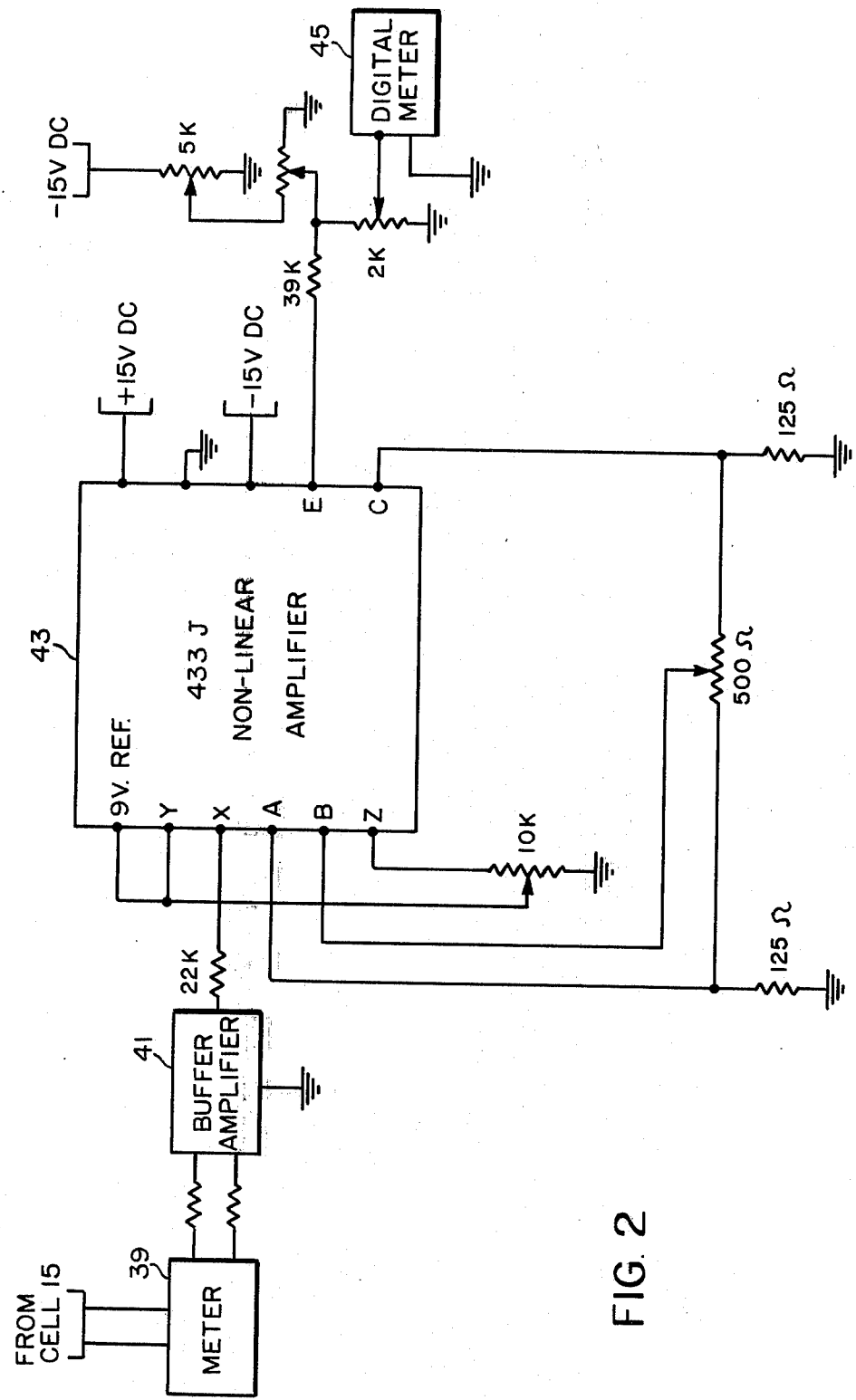
FIG. 2 is a detailed diagram of the measuring circuit of FIG. 1.

A preferred embodiment of a measurement circuit is shown in FIG. 2 and will now be described in further detail.

Known meter 39 circuitry is used to obtain a direct current voltage representative of the resistance of the water. A commercially available device compatible with the Barnstead B51 cell is the Barnstead PMC-51 resistivity meter. An external output is obtained from the meter circuitry 39 and is connected through a amplifier 41 to a non-linear amplifier 43. In the embodiment constructed by the applicant an Analog Device Model 433-J was used for non-linear amplifier 43 and arranged to have a output voltage representative of the input voltage raised to the minus 1.414 power. This function substantially tracks the concentration of organic carbon to the resistance as measured in the measuring chamber. The output is directed to a digital meter arrangement 45. Provision may be made to null the meter by means of a DC offset to compensate for background conductivity such as caused by free $CO_2$. The digital meter represents the amount of organic carbon, usually in units of parts per million (PPM).

For most measurements a standard volume of sample material of perhaps 1 milliliter is introduced into the system. Should the amount of organic carbon present in the sample be extremely low, 10 or 100 times the reference volume may be introduced. Provision may be made to shift the decimal point location accordingly in the digital meter read-out to eliminate ambiguities.

Figure 3:
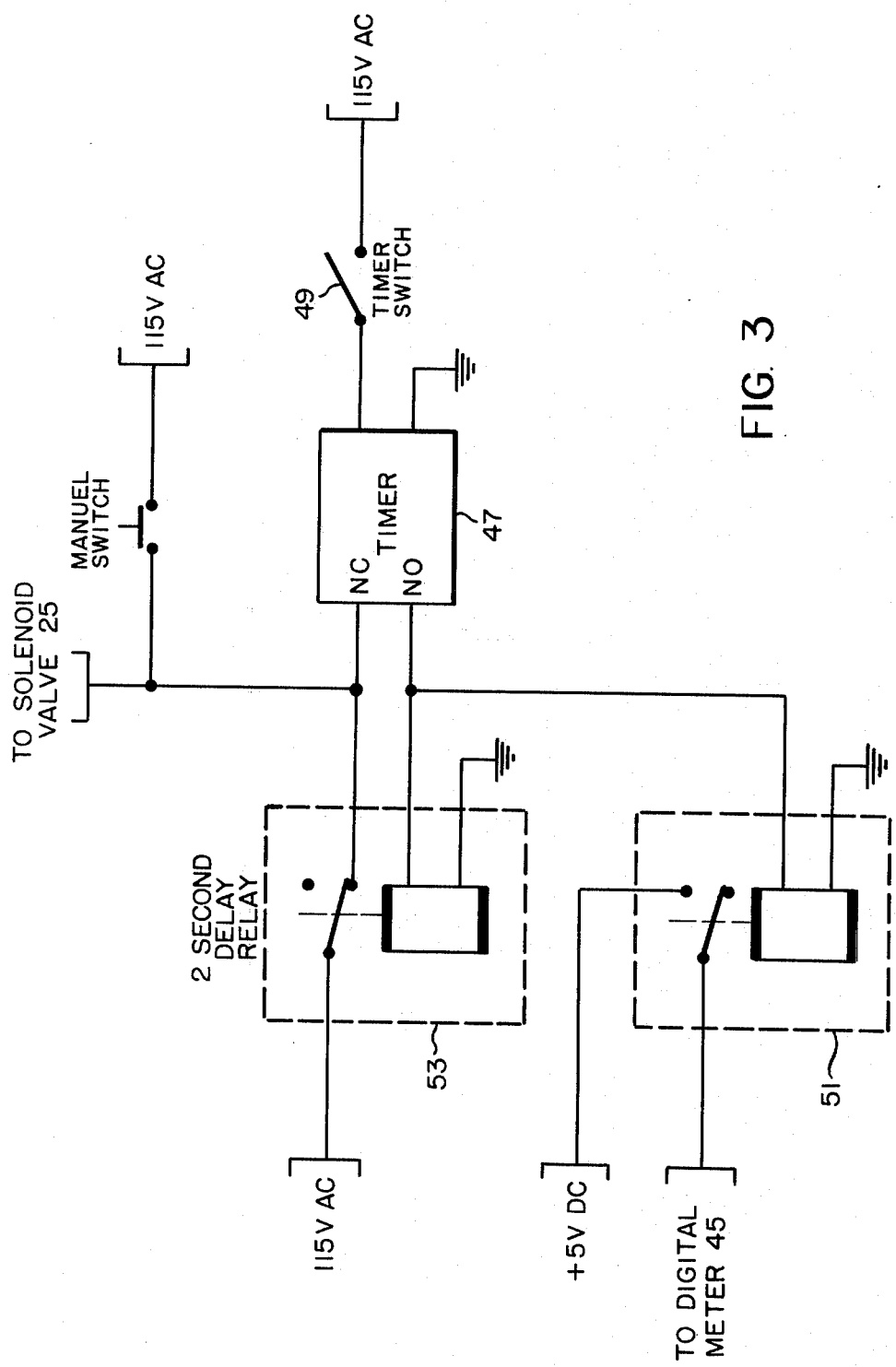
FIG. 3 is a detailed diagram of the timing circuit of FIG. 1.

Further in accordance with the invention, timing means (37 of FIG. 1) may be provided to time the oxidation cycle and then to purge the system to make it ready for measuring subsequent samples. The preferred construction of the timing means 37 is shown in FIG. 3.

A conventional industrial timer 47 provides a first voltage during the running of a time period and a second voltage when the time period has run.

In operation, the test sample is introduced into the system as hereinbefore set forth. The timer 47 is then activated by switch 49 and the time period begins to run. The timer 47 closes the solenoid water valve 25 removing the ion exchange 27 from the system and isolating the measuring compartment 11 from the first water loop 9. The time period is allowed to run during which time any organic carbon is converted to carbon dioxide. It has been found by the applicant that a time period of approximately 3 minutes is usually sufficient to convert substantially all of the organic carbon present. At the end of the time period a relay 51 is energized by the timer 47 to supply power to enable the digital voltmeter 45 while also giving the digital voltmeter a hold and read command so as to provide a readout of the PPM of carbon measured.

After a short delay, say 2 seconds after the running of the time period, a time delay relay 53 reopens the water valve 25 so as to start cleaning of the system in preparation for the next cycle. The cleaning may be monitored by means of the resistivity cell 15, after the resistance of the carrier water is sufficiently high. Alternatively a fixed time period of suffcient length of perhaps 5 minutes for the cleaning cycle may be used. In order to inform the operator of the status of the apparatus, an additional feature of the invention is the inclusion of indicating devices which may take the form of lamps (not shown) to indicate the completion of the various cycles.

The apparatus heretofore described will measure satisfactorily the content of organic carbon in aqueous solutions of many diverse organic compounds such as hydrocarbons, aliphatic and aromatic alcohols, ethers, starch, aromatic aldehydes, N-containing homo and hetero ring systems, and azo compounds. Accurate results at 0.01 ppm C are consistantly obtained with all organic compounds tested with the exception of urea.

Thus, it is apparent that there has been provided, in accordance with the invention, apparatus for measuring the content of organic carbon in aqueous solution, without the need for high temperature, catalysts or highly purified gases. While the invention has been described in conjunction with a specific embodiment thereof, it is evident that many alternatives modifications, and variations will be apparent to those skilled in the art in light of the foregoing description. Accordingly, it is intended to embrace all such alternatives, modifications, and variations as fall within the spirit and broad scope of the appended claims.

I claim:

1. Apparatus for measuring the amount of dissolved organic carbon introduced into a quantity of carrier water, said apparatus comprising:

a first housing
   a water pump;
   a first water loop containing said quantity of carrier water, including and interconnecting said pump and said first housing, for continually circulating said quantity of carrier water;
   means for introducing said dissolved organic carbon into said first water loop; an ultraviolet lamp in ultraviolet communication with the interior of said first housing for irradiating dissolved organic carbon present in said first housing producing thereby carbon dioxide;
   a second housing;
   an air loop interconnecting said first housing and said second housing for transferring a portion of said carbon dioxide produced in said first housing into said second housing and for supplying oxygen to said first housing; and
   measuring means for measuring the amount of carbon dioxide in said second housing said amount of carbon dioxide being representative of the amount of organic carbon introduced into the apparatus.

2. Apparatus as set forth in claim 1 wherein said ultraviolet lamp is at least partially internal to said first housing.

3. Apparatus as set forth in claim 1 wherein said air loop includes an eductor connected to said air loop and said first water loop.

4. Apparatus as set forth in claim 1 wherein said means for introducing said dissolved organic carbon through a rubber septum positioned in liquid communication with said first water loop for receiving said sample by means of a syringe and needle.

5. Apparatus as set forth in claim 1 wherein said measuring means includes a resistivity cell positioned in liquid communication with said second housing and a resistivity meter in electrical communication with said cell, said meter having a first output signal representative of the resistivity of the carrier water within said second housing, said resistivity being a function of the carbon dioxide transported from said first housing.

6. Apparatus as set forth in claim 1 which further includes a non-linear amplifier having an input being in electrical communication with said first output signal, said non-linear amplifier characterized by having a second output signal a function of said first signal raised to the minus 1.414 power.

7. Apparatus as set forth in claim 1 which further includes:

cleaning means for purifying said carrier water;
   a water valve capable of being opened and closed; and
   a second water loop interconnecting said pump, water valve, second housing, and first housing, whereby when said valve is open all of said carrier water in said apparatus is pumped through said cleaning means and when said valve is closed there is substantially no water flow between said first housing and said second housing.

8. Apparatus as set forth in claim 7 wherein said cleaning means is a mixed bed ion exchanger.

9. Apparatus as set forth in claim 7 which further includes timing means for closing said water valve for a time period sufficient for substantially all of said organic carbon to be oxidized into carbon dioxide and then upon the expiration of said period of time to open said valve so as to allow said cleaning means to purify said carrier water.

* * * * *